(12) United States Patent
Butsch

(10) Patent No.: US 6,730,087 B1
(45) Date of Patent: May 4, 2004

(54) BONE DISTRACTION DEVICE

(76) Inventor: Michael Butsch, Waldweg 32b, D-88718 Daisendorf (DE)

( * ) Notice: Subject to any disclaimer, the term of this patent is extended or adjusted under 35 U.S.C. 154(b) by 0 days.

(21) Appl. No.: 09/743,007

(22) PCT Filed: Jul. 1, 1999

(86) PCT No.: PCT/EP99/04540

§ 371 (c)(1),
(2), (4) Date: Mar. 2, 2001

(87) PCT Pub. No.: WO00/01315

PCT Pub. Date: Jan. 13, 2000

(30) Foreign Application Priority Data

Jul. 2, 1998 (DE) .......................... 198 29 523

(51) Int. Cl.[7] .............................................. A61B 17/66
(52) U.S. Cl. ........................................ 606/57; 606/105
(58) Field of Search ............................. 606/63, 64, 68, 606/90, 105, 57

(56) References Cited

U.S. PATENT DOCUMENTS

| | | | | |
|---|---|---|---|---|
| 5,156,605 A | * | 10/1992 | Pursley et al. | ............... 606/54 |
| 5,415,660 A | * | 5/1995 | Campbell et al. | ............... 606/62 |
| 5,626,581 A | * | 5/1997 | Staehlin et al. | ............... 606/63 |
| 5,704,938 A | * | 1/1998 | Staehlin et al. | ............... 606/62 |
| 5,961,553 A | * | 10/1999 | Coty et al. | ............... 623/16 |
| 6,033,412 A | * | 3/2000 | Losken et al. | ............... 606/105 |
| 6,500,177 B1 | * | 12/2002 | Martinelli et al. | ............... 606/57 |

FOREIGN PATENT DOCUMENTS

FR   2726460   *   5/1996   ........... A61B/17/72

* cited by examiner

*Primary Examiner*—Kevin Shaver
*Assistant Examiner*—Michael B. Priddy
(74) *Attorney, Agent, or Firm*—Bachman & LaPointe, P.C.

(57) ABSTRACT

A distraction device for moving apart a bone, present in one or more parts and possibly separated, so as to extend or bridge a bone fissure, comprising an intramedullary nail which can possibly be introduced into a medullary space of a bone and has at least two elements which can be axially displaced in relation to each other. To effect said displacement at least one working device is joined to the element and a movable retaining element which is supported on the element.

29 Claims, 5 Drawing Sheets

BONE DISTRACTION DEVICE

BACKGROUND OF THE INVENTION

The present invention relates to a distraction device for moving apart a one-piece or two-piece, possibly divided bone for lengthening or for bridging a bone gap, comprising an intra-medullary nail which can be introduced into a medullary cavity of a bone and which has at least two elements which can be moved axially relative to each other.

Such devices are known and available on the market in many different forms and designs. The aim of this distraction is endogenous reforming of bone substance. Reference may be made, for example, to EP 0 346 247 B1 which discloses an intracorporeal medullary nail which moves two parts of a bone in a mechanical manner. A disadvantage of this is that readjustment and tensioning are not readily possible.

In addition, DE 39 21 972 C2 discloses an intramedullary nail which can be lengthened likewise in a mechanical manner.

A disadvantage of the conventional distraction devices disclosed in the prior art is that they are in most cases too large and their effect is poor. They can transmit only limited distraction forces to the bone.

They are mostly of complex construction, difficult to operate, and very often have to be readjusted by surgical intervention, which is undesirable.

Moreover, such distraction devices known in the prior art are seldom suitable for very small bones, since their size is limited by complex structural parts.

The object of the present invention is to make available a distraction device of the above-mentioned type, with which high distraction forces are exerted in a controlled manner on the bone, and which can be used in any desired sizes for all extendable bones, including very small bones. It must be possible for distraction distances and distraction forces to be freely selected.

This object is achieved by the fact that at least one working device is connected to the element and to a movable holding element which is supported on the element.

SUMMARY OF THE INVENTION

In the present invention, elements are provided which are preferably inserted one within the other or guided one upon the other, and which are arranged to be displaceable. The elements are securely connected at the ends to the respective individual bone parts.

The stationary element is preferably provided with a push element on which the holding element moves axially to and fro. The holding element is supported on the outer element by means of a locking device. Here, widely differing embodiments of locking devices can be chosen. The holding element is connected at one end to the push element via a working device.

The working device, which preferably consists of wire defined in the axial direction or wound in the form of a spring, can change length considerably upon heating when so-called shape-memory alloys are used. The wire wound in the axial direction contracts by several percent of the total length and the spring becomes longer. The reciprocal support of the holding element on the two elements enforces the outward movement of one and/or the other element.

The working device is then cooled by interrupting a supply of current, and the wire can relax. A tensioning device, which is connected to the displaceable or movable element and the holding element, moves the holding element back counter to a direction.

Also preferably used as tensioning device is a wire element to which current is applied. By this means, the wire is heated and shortens since it is made of memory metal. The inner element is supported on the outer element via a locking device, so that the holding element can be moved in direction. The procedure is repeated.

Influence can be exerted with precision on the required distraction distance and distraction force via the number of wires fitted in working device and tensioning device, and via the corresponding distances from a receiving seat of the push element to the holding element and from the holding element to the inner element. Instead of the tensioning element, an extension spring element or compression spring element can also be used depending on configuration.

The wires which are used to heat the memory-metal wire are connected to energy transmitters which are arranged, for example, under the skin. In this way, the distraction device can be actuated over a long period of time inductively and in a contactless manner without operative outlay.

In all, the present invention makes available a distraction device which can be adapted in shape, size and technical configuration to any desired bone which is to be lengthened. Influence can be exerted with precision on the distraction behavior, for example, via the number of wires, via the length of the wires. This distraction device is also suitable for very high distraction forces in conjunction with the smallest possible insertion size.

BRIEF DESCRIPTION OF THE DRAWINGS

Further advantages, features and details of the invention will become evident from the following description of preferred illustrative embodiments and by referring to the drawing, in which.

DETAILED DESCRIPTION OF PREFERRED EMBODIMENT(S)

Figure 1:
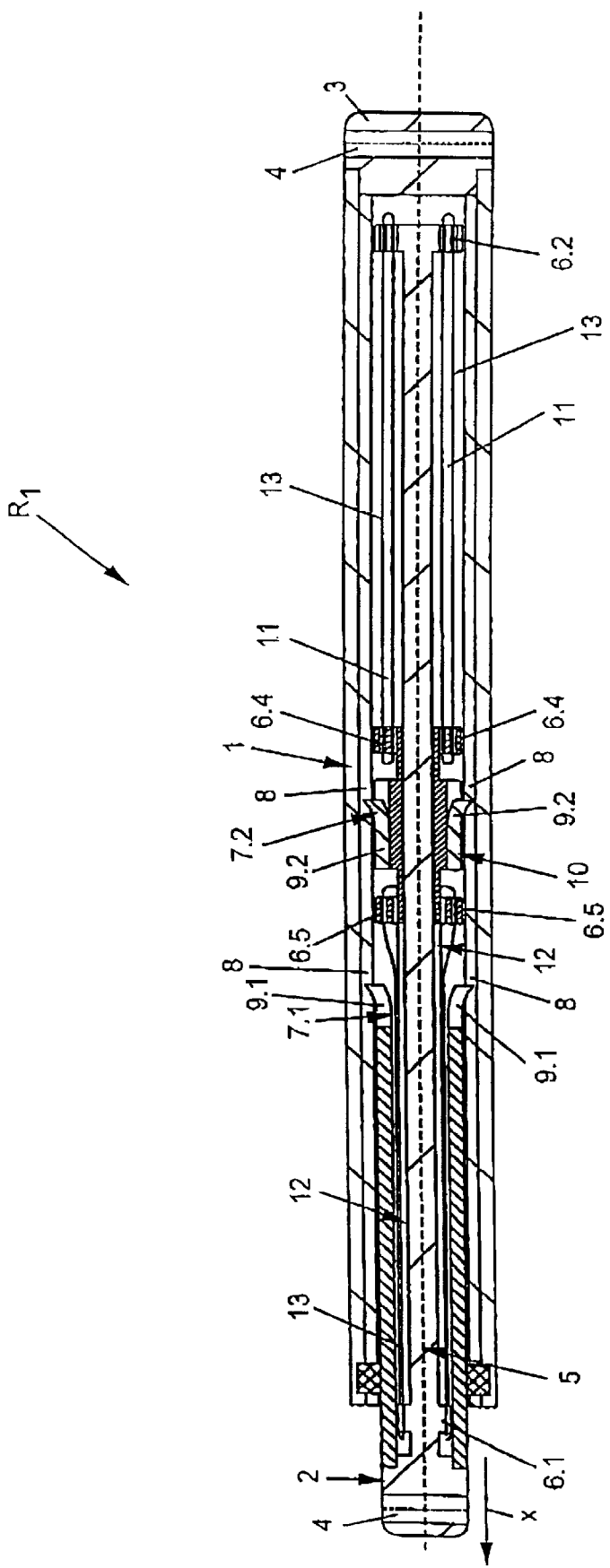
FIG. 1 shows an at least partially illustrated cross section through a distraction device according to the invention, with working device and tensioning device.

According to FIG. 1, a distraction device $R_1$ according to the invention has a tubular element 1 in which a matching element 2 is radially guided and is movable axially in a direction X. A cover 3 is provided as a closure at one end of the element 1. An opening 4 is provided in the cover 3 in order to fix the element 1 in a bone and anchor it there, for example by means of a screw element or the like.

A push element 5 is introduced into the element 2 at one end, which push element 5, at a protruding end, is likewise provided with an opening 4 for fixing in a bone. The push element 5 is connected to the element 2 in a preferably fixed manner.

The push element 5 is provided with a receiving seat 6.1 which is preferably arranged near the opening 4. In the element 1, the push element 5 likewise has a receiving seat 6.2 at the other end near the cover 3.

Preferably directed inwards at the end, the element 2 is provided with a locking device 7.1 which engages by means of a locking element 9.1 in recesses 8 not shown in detail here. The locking device 7.1, in particular the locking elements 9.1, are designed in such a way that they engage in the recesses 8 of the element 1, and only a movement of the element 2 in a direction X and/or a movement of the element 1 counter to the direction X is possible. The push element 5 is preferably longer than the element 2.

According to the illustrative embodiment of the present invention, a holding element 10 is arranged inside the element 1, which holding element 10 is likewise provided with a locking device 7.2. The holding element 10 is axially guided on the push element 5. This locking device 7.2 likewise has locking elements 9.2 which engage in corresponding recesses 8 provided inside the element 1. The holding element 10 can be moved axially to and from inside the element 1. When the holding element 10 is moved in the direction of the cover 3, the locking elements 9.2 engaging in the recesses 8 of the element 2 entrain the element 1 in the axial direction counter to a direction X. The locking pawls 9.1 engage without locking over the recesses 8. When the holding element 10 is moved back in the opposite direction, the element 2 is prevented from moving back axially by means of the locking elements 9.1 of the stationary element 2 engaging in the recesses 8, and the locking elements 9.2 engage without locking over the recesses 8. The holding element 10 is provided on both sides with receiving seats 6.4 and 6.5.

In the present invention, a working device 11 is fitted between holding element 10 and push element 5, in particular between their receiving seats 6.2 and 6.4. Moreover, a tensioning device 12 is fitted between the element 2, in particular the receiving seat 6.1, and the holding element 10, in particular its receiving seat 6.5, and connects the holding element 10 to the element 2.

In the present illustrative embodiment, the working device 11 is formed by a wire 13 which is wound around the receiving seats 6.2 and 6.4. The wire 13 is preferably made of shape-memory metal, also known as memory metal. The wires 13 are wound without electrical contact or provided with an insulation and can be fed with current from outside.

In the present illustrative embodiment, the tensioning device 12 consists of the wire 13 made of memory metal. This wire is preferably wound around the receiving seat 6.1 of the element 2 and receiving seat 6.5 of the holding element 10.

This distraction device $R_1$ is introduced in a known manner into a bone to be lengthened for bone-bridging or bone-lengthening. The two elements 1, 2 are connected securely to the corresponding bone parts (not shown here), by, for example, securing elements engaging through the openings 4 of the elements 1, 2.

For distraction, the working device 11 is put into operation. To do this, current is applied to the wire 13 or to a plurality of wires, so that these wires heat as a result of a low cross section and a high ohmic resistance. The result of this heating is that the wires made of memory metal contract above a defined temperature, the so-called limit temperature. The greater the distance between the receiving seat 6.2 and 6.4 of push element 5 and holding element 10, the greater is the shortening of the wires 13 on heating of the working device 11. This shortening has the effect that the push element 5, under the effect of pressure and via the receiving seats 6.2., 6.4., moves the element 2 in the direction X out of the element 1. In the process, the holding element is supported on the element 1 by means of the locking device 7.2, so that a return movement is suppressed. The locking elements 9.2 then preferably engage in recesses 8 of the element 1.

In this way, influence can be exerted on the distraction via the choice of the wire 13, via the distance between the receiving seats 6.2 and 6.4. Correspondingly, the distraction forces here can also be exactly calculated and defined by the number of wires.

The current supply is then interrupted and the working device 11 cools. The wires 13 relax.

The tensioning device 12 is then put into operation, for example by application of current, so that its wires 13, which are arranged between the receiving seat 6.1 and 6.5 of the holding element 10, heat and shorten in the manner described above, as they are made of memory metal. This shortening causes a return of the holding element 10, with the movement described above. At the same time, the wires 13 of the working device 11 are tensioned again.

This procedure can be repeated as often as desired. In this way, the element 2 can be withdrawn from the element 1 and/or the element 1 can be withdrawn from the element 2. In the context of the present invention, however, it should also be possible to configure the elements 1, 2 as solid profiles, rectangular profiles or the like.

Also in the context of the present invention, it should be possible for the elements 1, 2 to be moved relative to one another only axially and not radially. This can be achieved, for example, by means of guide grooves or the like.

Figure 2:
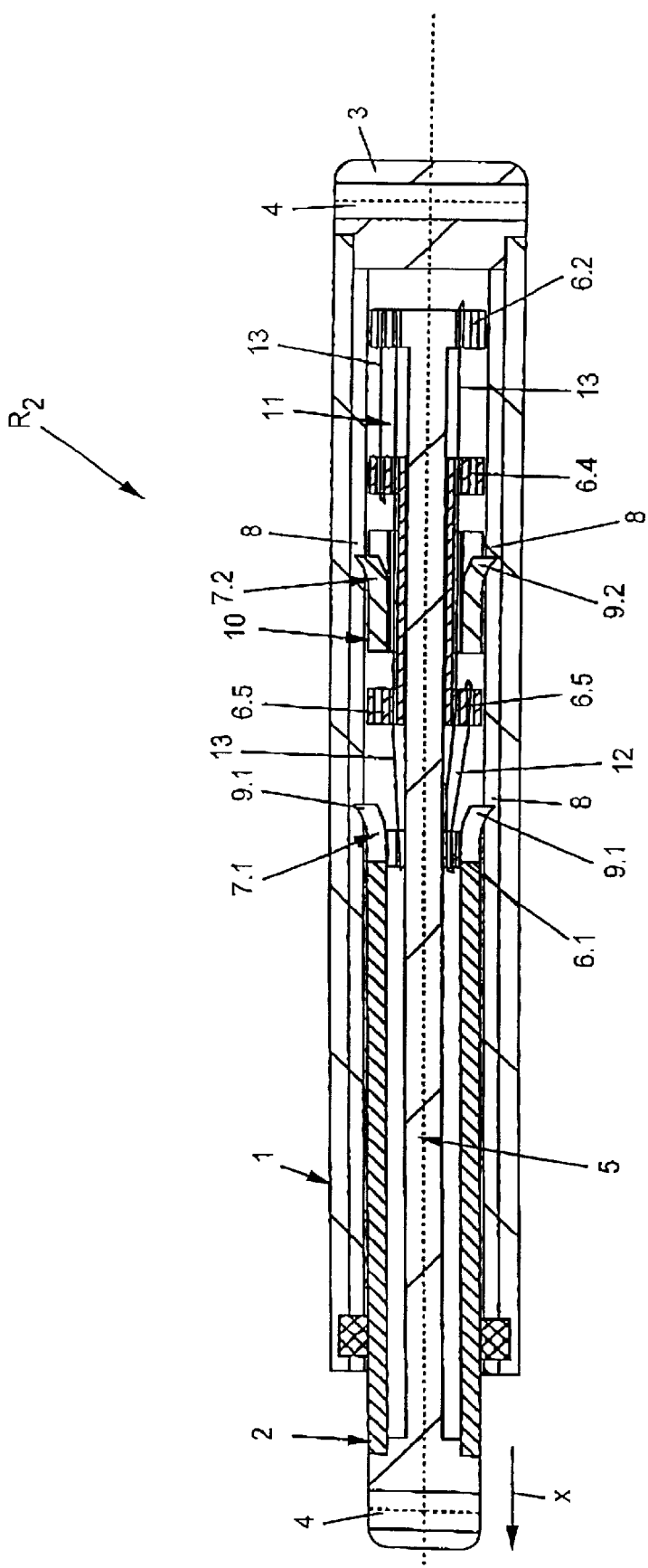
FIG. 2 shows a cross section through a further illustrative embodiment of the distraction device according to FIG. 1.

In a further illustrative embodiment of the present invention according to FIG. 2, a distraction device $R_2$ is shown whose structure substantially corresponds to the distraction device $R_1$ according to FIG. 1. By diverting the wires 13 of the working device 11 and of the tensioning device 12, a particularly short structure is obtained. This is advantageous for example for very small and short tubular bones in the hand region.

The receiving seat 6.5 on the element 2 is therefore arranged in the area of the locking device 7.1. This has the additional advantage that very small distraction steps cat be taken and the distraction device $R_2$ as a whole can be made very small. This is advantageous for example for very small and short bones.

The mode of functioning of this distraction device $R_2$ corresponds to that described above.

Figure 3:
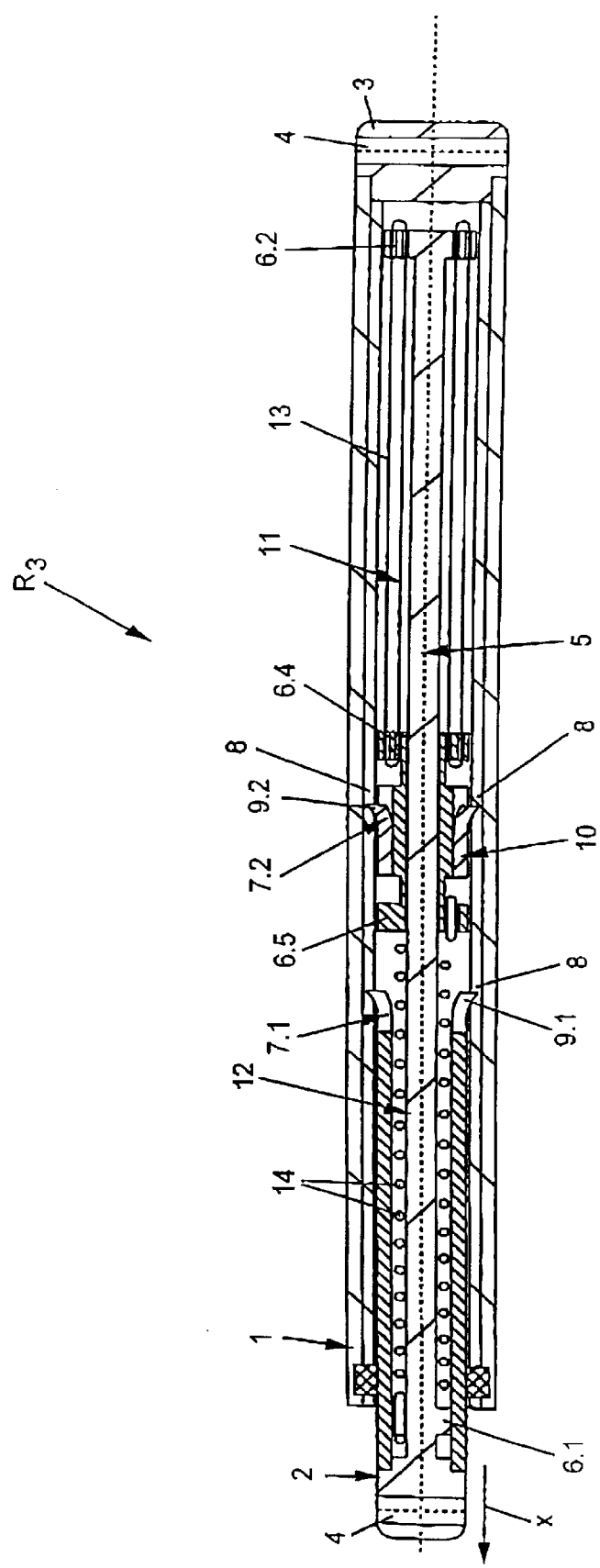
FIG. 3 shows a cross section through a distraction device according to FIGS. 1 and 2, with an extension spring as tensioning element.

In a further illustrative embodiment of the present invention according to FIG. 3, a distraction device $R_3$ is shown which corresponds approximately to the distraction device $R_1$ according to FIG. 1. Only the tensioning device 12 is designed as an extension spring element 14. The wires 13 can be omitted here. The extension spring element 14 is fixed at one end on the receiving seat 6.1 of the element 2 and at the other end on the receiving seat 6.5 of the holding element 10.

When the working device 11 is put into operation, after the wires 13 have been heated the push element 5 is moved relative to the fixed and latched holding element 10 in direction X and at the same time the extension spring element 14 is tensioned. In the manner described above, the locking elements 9.2 entrain the element 1 in the axial direction.

After the supply of current has been interrupted, the working device 11 can cool. The tensioned extension spring element 14 extends the wires 13 to their original length. The mode of functioning of the locking elements during the return is the same as with the distraction device $R_1$. In this way, the element 2 can be moved out relative to the element 1.

In the context of the present invention, however, it should also be possible, for example, for the elements 1, 2 to be designed as round or polygonal, rectangular hollow profiles and for them to be displaceable one inside the other. The elements 1, 2 can also be designed, however, as solid profiles which can be displaced relative to one another.

Figure 4:
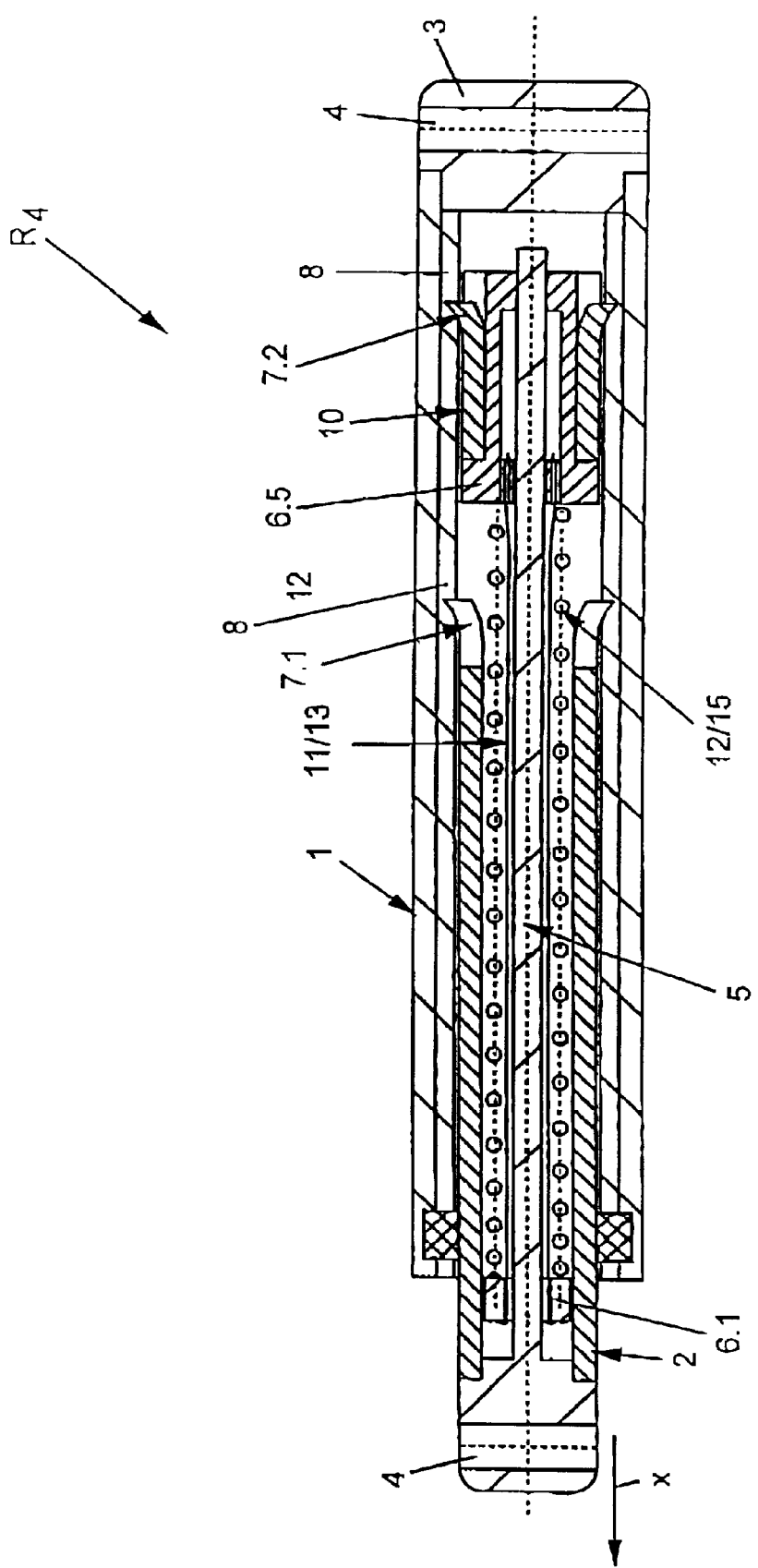
FIG. 4 shows a cross section through a distraction device according to FIG. 3, with a compression spring as working device.

In a further illustrative embodiment of the present invention according to FIG. 4, a distraction device $R_4$ is shown in which the working device 11 and the tensioning device 12 are fitted between the holding element 10, in particular its receiving seat 6.5, and the receiving seat 6.1 of the element 2. This therefore permits a very short axial construction. On heating above a limit temperature, the wire 13 of the tensioning device 12 is tensioned and tensions a compression spring element 15 of the working device 11. As a result, the holding element 10 is entrained in the direction X shown there. This permits the ratchet mechanism described in FIG. 1.

After cooling, the compression spring element 15 can relax and axially entrains the element 1 and/or the element 2 counter to or in the direction X shown there. The wires 13 are simultaneously stretched to their original length.

In this illustrative embodiment, the push element 5 is axially force-free and serves only for guiding the holding element 10.

Figure 5:
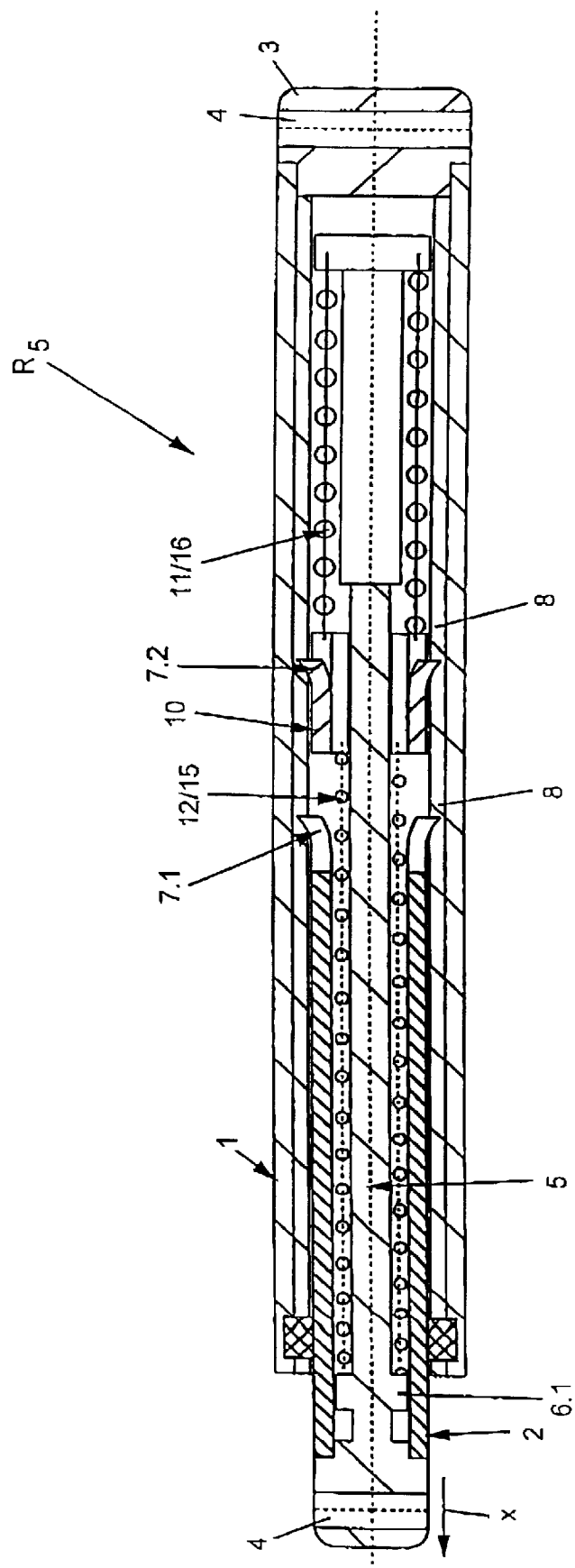
FIG. 5 shows a cross section through a distraction device according to FIG. 4, with a compression spring element made of shape-memory material as working device and a compression spring as tensioning device.

In the illustrative embodiment of the present invention according to FIG. 5, a distraction device $R_5$ is shown in which the working device 11 as compression spring 16 instead of the wire 13 of shape-memory metal is wound into a spring which is lengthened when a defined limit temperature is exceeded. As a result, a compression spring element 15 of the working device 12 is tensioned. In the cooled state of the compression spring 16, the forces can cause the working device 12 to contract to its original length. The corresponding mode of functioning of the ratchet mechanism, as is described above, remains the same.

The concept of the present invention should also include the possibility that the wires 13, made of memory metal, are provided with insulation permitting corresponding shortening and extension of the wire 13. As a result of the small cross section of the wires 13, application of current causes heating. As the wires 13 are made of memory metal, this heat is utilized to shorten the wires 13. The wires 13 of the working device 11 and tensioning device 12 are connected, via devices not shown here, to the energy supply, which lies for example in the area under the skin. The electrical energy for putting the distraction devices $R_1$ to $R_5$ into operation can then be transmitted via corresponding inductive transmitters. Information concerning the distraction can also be conveyed in this way.

The wires 13 or other elements of the distraction device can also be inductively heated directly from outside, without, for example, having to provide an energy transformer. This can be achieved, for example, with an alternating electro-magnetic field which is applied to the extremities from outside. Electronic control or regulation can be omitted.

It should also be possible to assign corresponding temperature sensors to the distraction devices $R_1$ to $R_5$, in particular the working device 11 and tensioning device 12, in order to permit exact temperature control and regulation. At the same time, the temperature sensors can be used to monitor whether cooling upon relaxation of the working device after heating has taken place. Only then is the tensioning device 12 put into operation.

In addition, such temperature sensors can be used to effect alternating application of current to the working device 11 and tensioning device 12, in which case the corresponding switching operations can be counted to calculate the distraction distance achieved.

It can also be advantageous to provide electrical or mechanical contact elements for the respective end position of the holding element 10, for example upon shortening by means of the working device or upon tensioning by means of the tensioning device 12. The corresponding contact elements can be used for alternating application of current to working device 11 and tensioning device 12 and for counting the contacts and calculating the distraction distance achieved.

In addition, absolute distance measurement can be provided via a length measurement system which functions, for example, according to the physical principle of electric induction, magnetostriction, magnetoresistance, or the change in the electrical resistance with increasing length of the extended elements 1, 2.

To determine the lengthening of a bone or for bridging a bone gap, force sensors for monitoring the distraction forces can also be provided. In this way, influence can also be exerted on the lengthening of a bone.

| Reference numbers | |
|---|---|
| 1 | Element |
| 2 | Element |
| 3 | Cover |
| 4 | Opening |
| 5 | Push element |
| 6 | Receiving seat |
| 7 | Locking device |
| 8 | Recess |
| 9 | Locking element |
| 10 | Holding element |
| 11 | Working device |
| 12 | Tensioning device |
| 13 | Wire |
| 14 | Extension spring element |
| 15 | Compression spring element |
| 16 | Compression spring |
| R1 | Distraction device |
| R2 | Distraction device |
| R3 | Distraction device |
| R4 | Distraction device |
| R5 | Distraction device |
| X | Direction |

What is claimed is:

1. A distraction device comprising a first element (1) and a second element (2), a holding element (10) engages on the first element (1), at least one working device (11) connected to the second element (2) and to the holding element (10), a tensioning device (12) fitted between the holding element (10) and the second element (2), means for contracting the at least one working device (11) for moving the first element (1) and second element (2) axially relative to each other in a first direction, and means for contracting the tensioning device for moving the first element (1) and the second element (2) axially relative to each other in a second direction opposite to the first direction.

2. A distraction device according to claim 1, wherein the second element (2) has a push element (5) fixed thereto.

3. A distraction device according to claim 2, wherein the push element (5) is provided at one end with a receiving seat (6.2).

4. A distraction device according to claim 3, wherein the working device (11) is arranged between the receiving seat (6.2) of the push element (5) and the holding element (10).

5. A distraction device according to claim 3, wherein the working device (11) is made of at least one wire element (13), the wire element (13) being made of shape-memory material.

6. A distraction device according to claim 5, wherein the at least one wire (13) of the working device (11) is guided through the holding element (10) and the at least one receiving seat (6.1 to 6.5).

7. A distraction device according to claim 1, wherein locking devices (7.1, 7.2) are provided on each of the holding element (10) and the second element (2), the locking devices comprise recesses (8) in the first element with locking elements (9.1, 9.2) on the holding element and the second element for engaging therein, wherein the locking devices (7.1, 7.2), by means of force transmission from the holding element (10) to the second element (2), prevent the first element (1) from moving in one direction.

8. A distraction device according to claim 7, wherein the second element (2) is arranged so that it can be displaced along the first element (1).

9. A distraction device according to claim 8, wherein the locking element (7.1) is positioned on the second element to prevent a return movement of the second element (2) relative to the first element (1).

10. A distraction device according to claim 1, wherein the first and second elements (1,2) are designed as hollow profiles, the second element (2) being displaceably arranged inside the first element (1).

11. A distraction device according to claim 1, wherein the working device (11) is made at least partially of shape-memory material.

12. A distraction device according to claim 1, wherein, by actuation of the working device (11) by the means for contracting, the push element (5) of the second element (2) is moved toward the holding element (10).

13. A distraction device according to claim 1, wherein the means for contracting the working device (11) comprises heating means applied to the working device (11) for shortening of the working device (11).

14. A distraction device according to claim 13, wherein, by shortening of the working device (11), the push element (5) and the second element (2) can be moved in direction (X) relative to the holding element (10) fixed on the first element (1).

15. A distraction device according to claim 1, wherein the tensioning device (12) is made at least partially of shape-memory material and is provided between a receiving seat (6.1) of the second element (2) and a second receiving seat on the holding element (10).

16. A distraction device according to claim 15, wherein the means for contracting comprises heating means for heating the tensioning device (12), which heating effects a shortening of the tensioning device (12).

17. A distraction device according to claim 10, wherein the shortening of the tensioning device (12) allows the holding element (10) to be moved relative to the second element (2) in the direction (X).

18. A distraction device according to claim 17, wherein the tensioning device (12) when cooled is extended.

19. A distraction device according to claim 1, wherein the tensioning device (12) is formed by a plurality of wires (13) which are insulated front each other, the wires (13) being made of a shape-memory material.

20. A distraction device according to claim 1, including means for alternately actuating the working device (11) and tensioning device (12).

21. A distraction device according to claim 1, wherein the means for contracting is associated with both the working device (11) and the tensioning device (12).

22. A distraction device according to claim 1, wherein the working device (11) and the tensioning device (12) are designed as tubular elements made of shape-memory metal, and a heating device is associated with both for contracting same.

23. A distraction device according to claim 1, wherein the working device (11) and tensioning device (12) are supplied with energy for heating by the means of contracting in a contactless manner.

24. A distraction device according to claim 1, wherein the first and second elements (1, 2) are associated with contact elements for detecting end positions of the holding element (10) and the first element (1).

25. A distraction device according to claim 1, wherein force sensors for monitoring the distraction forces are associated with the first and second elements (1, 2), the tensioning device (12), and the working device (11).

26. A distraction device according to claim 1, wherein the tensioning device (12) and the working device (11) are provided between the first and second elements and holding element (10).

27. A distraction device according to claim 1, wherein at least one compression spring (16) is provided between the second element (2) and the holding element (10), and at least one compression spring element (15) is provided between holding element (10) and push element (5).

28. A distraction device according to claim 27, wherein both compression spring elements are made of shape-memory material.

29. A distraction device according to claim 1, wherein the working device (11) and tensioning device (12) are heated by a single means for contracting.

* * * * *